(12) United States Patent
Kalyuzhnaya et al.

(10) Patent No.: US 6,631,649 B1
(45) Date of Patent: Oct. 14, 2003

(54) SYSTEM FOR MEMBRANE REMOVAL AND TRANSFER

(75) Inventors: Galina G. Kalyuzhnaya, Roseville, MN (US); Daniel L. Nestor, Woodbury, MN (US)

(73) Assignee: MVS Pacific, LLC, Minneapolis, MN (US)

( * ) Notice: Subject to any disclaimer, the term of this patent is extended or adjusted under 35 U.S.C. 154(b) by 0 days.

(21) Appl. No.: 10/142,701

(22) Filed: May 9, 2002

Related U.S. Application Data

(60) Provisional application No. 60/289,874, filed on May 9, 2001.

(51) Int. Cl.[7] .................................................. G01N 1/00
(52) U.S. Cl. .................................. 73/863.31; 73/864.45
(58) Field of Search ............ 73/863.23, 864.41–864.45, 73/863.31; 83/919, 618, 620; 30/358, 362, 363

(56) References Cited

U.S. PATENT DOCUMENTS

| | | | | |
|---|---|---|---|---|
| 1,517,931 A | * | 12/1924 | Wible | ........................... 30/358 |
| 3,500,710 A | * | 3/1970 | Taber | ........................... 83/588 |
| 3,785,194 A | * | 1/1974 | Bradlee | ................... 72/405.13 |
| 4,036,088 A | | 7/1977 | Ruskin | |
| 4,688,457 A | | 8/1987 | Neilsen et al. | |
| 4,713,995 A | | 12/1987 | Davi | |
| 4,974,462 A | | 12/1990 | Rising et al. | |
| 5,146,794 A | | 9/1992 | Rising et al. | |
| 5,156,074 A | * | 10/1992 | De Ros et al. | ............... 83/100 |
| 5,575,188 A | * | 11/1996 | Hu | .............................. 83/167 |

\* cited by examiner

Primary Examiner—Robert Raevis

(57) ABSTRACT

A filter removal apparatus for removal of microporous filter membranes from multi-well filtration plate comprises a removal device and a pusher having defined therein a plurality of vertical pushpins. The pusher has a leading pushing surface to which elongated pushpins are secured each having a flat face to deliver an even pressure onto the filter membrane. The removal device comprises a stationary base plate with end wall and side walls holding a pivotal cylindrical bar which rotates in eccentric manner along its longitudinal axis. Rotation of cylindrical bar using attached handle approximately 180 degrees around the longitudinal center-line of pivot shafts causes the cylindrical bar to rotate in an eccentric motion, thus imparting a linear force to a moving plate which forces the pusher into the filter plate and causing removal of filter membranes and their flattening onto adhesive film for retention.

3 Claims, 5 Drawing Sheets

SYSTEM FOR MEMBRANE REMOVAL AND TRANSFER

CROSS-REFERENCE TO RELATED APPLICATION

This application claims the benefit of Provisional Patent Application 60/289,874 filed May 9, 2001.

CROSS-REFERENCE TO RELATED APPLICATIONS

Provisional Patent Application Ser. No.: OC0000000063 11882

BACKGROUND OF THE INVENTION

1. Field of Invention

The present invention relates to a filter membrane pusher construction and a system that utilizes such pusher to remove filter membranes with biological samples retained by filters from multi-well filtration plate generally and, more particularly, but not by way of limitation, to a novel non-destructive collection of filter-retained biological specimens including cells and tissues for their further examination and storage.

2. Background Art

Filtration plates containing microporous membrane filters are widely used in basic research and for high throughput biological testing. The incorporation of membrane filters into the bottom of 96-well plates allows exploiting the capabilities of 96-well formats including automated liquid handling and recording of multiple experimental data. Membrane-bottom microplates allow multiple sequential procedures (i.e. sample preparation, cell growth and fixation, and washing) to be performed rapidly within a single plate. Because of this, 96-well membrane-bottom plates (i.e. MultiScreen plates manufactured by Millipore Corporation and AcroWell plates manufactured by Pall Corporation) are widely used for high-throughput cell-based assays (lymphocytes, hybridomas) including large-scale screening of natural and/or synthesized products to determine their biological activity or toxicity. When plates are used to grow and collect cells on the filter membranes the latter need to be removed from the plates at the end of experiment (i.e. immunohistochemistry, in situ hybridization or laser microdissection) since cells attached to the membranes can be accurately investigated only using high-magnification microscopy which cannot be done on membranes attached to the plate. It is important that removal of filter membranes should not affect morphology of membrane-retained cells and tissues and cause their loss.

Another use of 96-well membrane-bottom microplates includes an enzyme-linked immunospot assays (elispot) to retain proteins released by cultured cells on the membrane and subsequently detect such proteins by staining them. Upon completing elispot experiments, membrane filters with stained protein spots need to be removed from the plate to quantify spots by high-magnification image analysis and for proper membrane storage (i.e. removed membranes can be laminated for protection). Since particles of the dye used to stain proteins are loosely attached to the filter membrane, the removal of membranes has to be done to avoid the detachment of dye particles from the membrane.

Filter punch constructions are disclosed in U.S. Pat. No. 4,974,462 to Rising and Montminy and in U.S. Pat. No. 5,146,794 to Rising et al. These punches allow removing filters from multi-well filtration plates. However, these filter punches utilize a sharp central piercing member that punctures the filter, and hence cannot be used for a non-destructive collection of biological specimens such as cells and tissues. In addition, those filter punches do not permit to flatten punched membranes onto adhesive film, since piercing member will be making a hole rather than evenly push on underlying materials.

Other punch devices are disclosed in U.S. Pat. No. 4,036,088 to Ruskin, U.S. Pat. No. 4,713,995 to Davi and U.S. Pat. No. 4,688,457 to Neilsen and Davi. These devices are designed for punching holes in paper. These punch devices cannot be used for punching filter membranes from multi-well filtration plates for two reasons. First, a paper insertion gap is too narrow to accommodate a filtration plate, and second, punches have concave punching surface and hence will not permit flattening of punched material onto underlying support.

Accordingly, it is a principal object of the present invention to provide means and method for a non-damaging removal of filter membranes with deposited specimens from filtration plates.

It is a further object of the invention to provide means and method for immediate transfer and flattening of removed filter membranes onto adhesive support for retention.

It is a further object of the invention to provide means and method for simultaneous removal of all filter membranes from a plurality of wells and simultaneous transfer of all removed filter membranes onto adhesive support.

Other objects of the present invention, as well as particular features and advantages thereof, will be elucidated in, or apparent from, the following description and the accompanying drawings.

SUMMARY OF THE INVENTION

The present invention provides a pusher and a removing system for non-destructive removal of filters with retained biological samples from multi-well filtration plates. The pusher comprises a holder and a plurality of pushpins extending from the holder and perpendicular to it. Each pushpin has a round flat face-leading surface to provide an even distribution of pressure over the surface of underlying filter membrane and covering the most of the section of the filter membrane which is not attached to the well. Pushpins are aligned to match corresponding wells in the multi-well filtration plate. After the pusher is plugged into the multi-well filtration plate such assembly is inserted into the opening of the removal device where removal of filter membranes and their immediate transfer onto adhesive support will take place. The removing device comprises a base member and represents lower (steady) and upper (moving) platforms between which the aforementioned assembly of plate and pusher will be placed. Using a lever connected to the upper platform, the operator applies pressure over the pusher plate forcing its multiple pins into corresponding wells. During the operation, pressure pins of the pusher plate first detach the membranes from the wells and then these pressure pins press membranes against the adhesive support glued to the bottom of the membrane-backed plate. After completing the membrane-removing procedure, the membrane-backed plate with plugged-in pusher plate is removed from the membrane-removing device. After that adhesive support with individual membranes attached to it is pealed of the membrane-backed plate. This invention provides researchers who use membrane-backed plates with the tool that facilitates collection, analysis and storage of multiple membranes after completing the experiment. This system is alternative to laborious and tedious single-pin manual membrane removal procedure that cause damage to membranes which, in turn, results in loss of valuable experimental data. In addition, the system is user-friendly and does not require any specific training on the part of the operator. Furthermore, our system allows the shortening of membrane removal time and thus makes this a device of choice for researchers who run high-throughput assays using membrane-backed plates.

DRAWINGS

REFERENCES NUMERALS IN DRAWINGS

| 1 | base plate | 20,21 | cylindrical pivot shafts |
|---|---|---|---|
| 2 | moving plate | 22 | pusher |
| 3,4 | side walls | 22a | holder |
| 5 | end wall | 22b | pushpins |
| 6,7 | plate guides | 22c | flat face |
| 8 | elastic pad | 30 | well |
| 9 | wear pad | 31 | filter membrane |
| 10 | cylindrical bar | 32 | adhesive film |
| 11 | handle | 33 | elastic pad |
| 12,13,14,15 | compression springs | 34 | filter punch |
| 16,17,18,19 | guide pins | 35 | piercing member |

DESCRIPTION

The pusher and the removal device will now be described in greater detail with reference to the above drawings, which show the pusher and the removal device.

Figure 1:
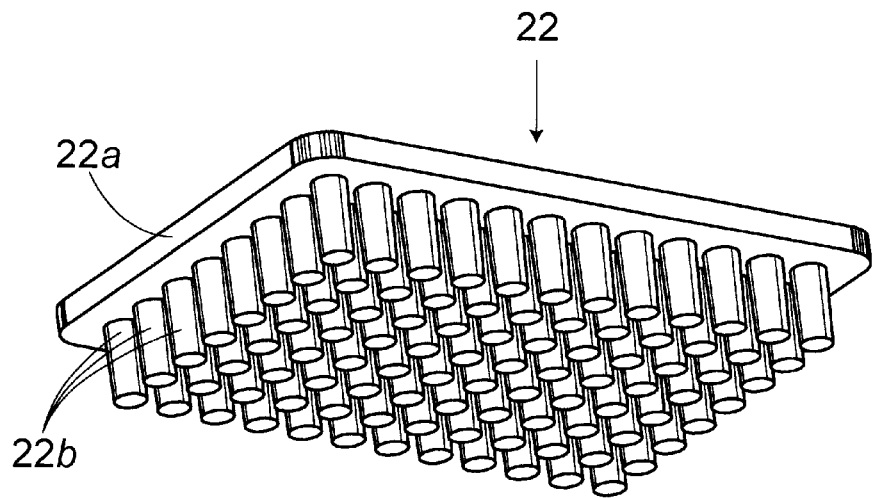
FIG. 1 shows a perspective view of a pusher according to the invention.
Figure 2:
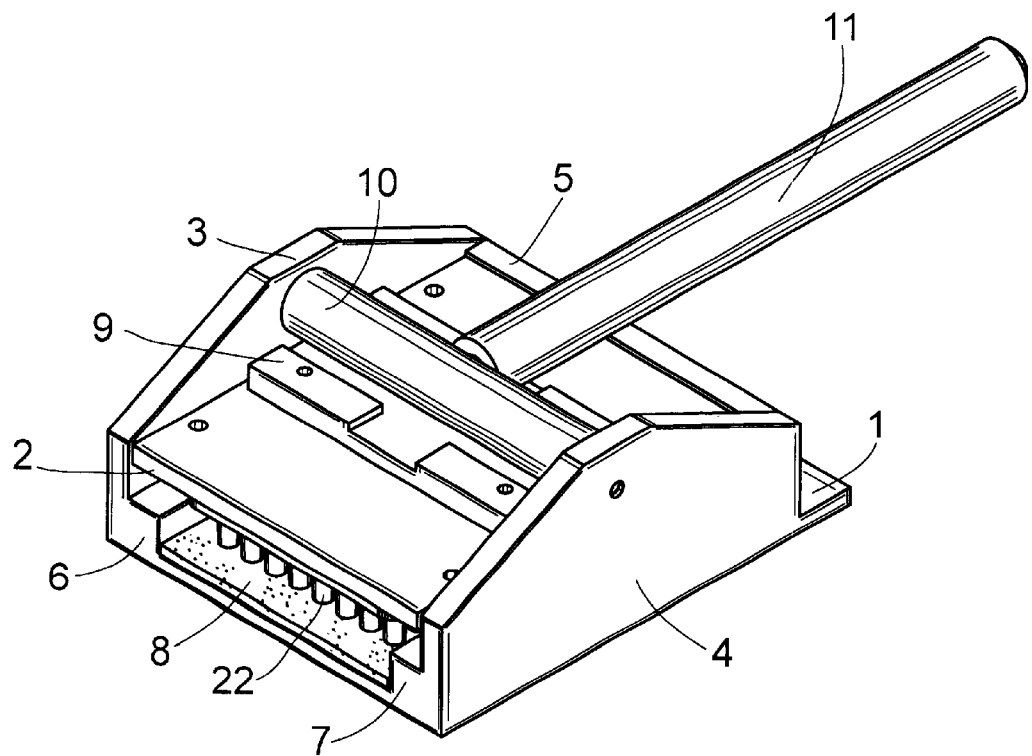
FIG. 2 shows perspective view of a removal device.
Figure 3:
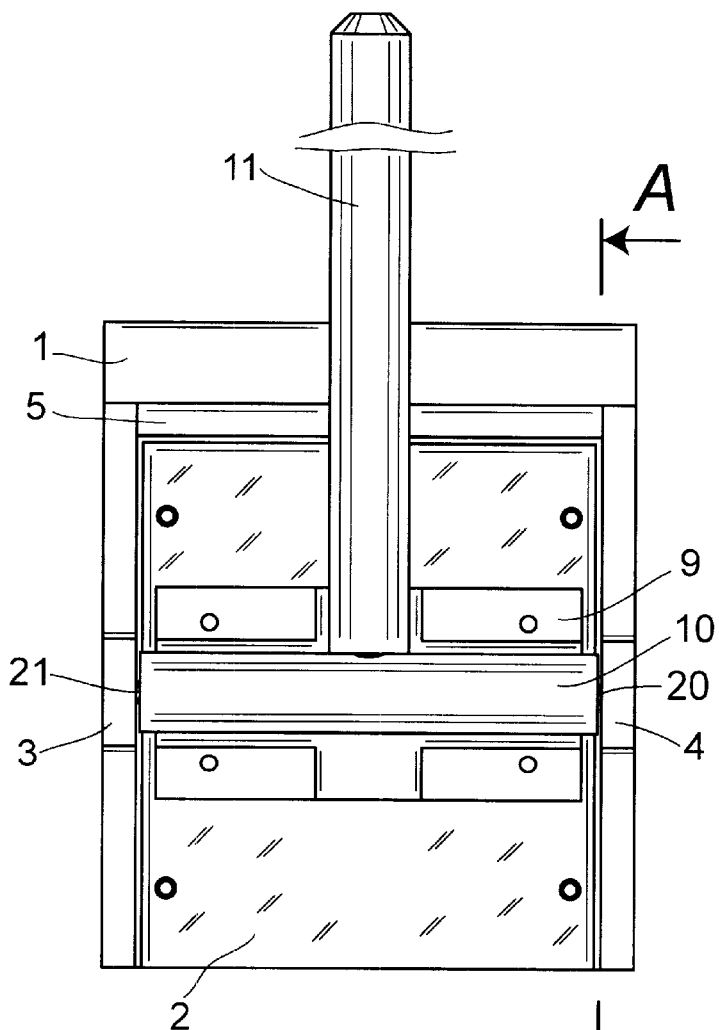
FIG. 3 shows a top view of the removal device.

A preferred embodiment of the pusher is shown in FIG. 1. The pusher 22 is comprised of cylindrical pushpins 22b extending perpendicular from a holder 22a. The diameter, quantity and location of cylindrical pushpins 22b attached to the holder 22a are determined by the diameter, quantity and location of the wells in the multi-well filtration plate from which filter membranes will be removed. Generally, cylindrical pushpins 22b are located and sized in such a way that all pushpins 22b can simultaneously enter and pass through their corresponding wells in the multi-well filtration plate. Pushpins 22b can be secured to the holder 22a by any means.

However, it is preferred that the holder 22a and pushpins 22b are molded as one piece.

The removal device shown by the way of example in FIGS. 2–6 comprises two opposing planar side walls 3,4, and a planar end wall 5, mounted on top and perpendicular to the planar surface of a base plate 1. Two opposing plate guides 6,7, are extends from the base plate 1, and are adjacent to the planar side walls 3,4 respectively. It is understood that base plate 1, side walls 3,4,5, and plate guides 6,7 can be assembled by any means but it is preferred them to be casted in one piece to withstand a substantial amount of mechanical stress.

A generally planar flexible elastic pad 8 rests on the top surface of the base plate 1, between the plate guides 6,7. A compression spring 12, is radially centered over a cylindrical guide pin 16, which extends vertically from, and disposed near the end of the top surface of guide 6. Compression spring 13 and Compression spring 13 are similarly disposed near the opposite end of guide 6. Guide 7 is similarly configured using compression springs 14,15 and guide pins 18,19 respectively. A movable plate 2 rests on compression springs 12,13,14,15. Guide pins 16,17,18,19 pass through corresponding holes in plate 2, thus allowing upper moving plate 2 to move longitudinally along guide pins 16,17,18,19, and generally maintaining approximate parallelism between plate 2 and base plate 1. Enough clearance is provided in the four holes in plate 2 to allow it to float somewhat out of parallel with base plate 1. A wear pad 9 is mounted to the top surface of the moving plate 2. Two cylindrical pivot shafts 20,21, protrude longitudinally from each end of a generally cylindrical bar 10, and are radially offset from this bar. Both pivot shafts 20,21, pass through holes in the side walls 3,4 respectively thus supporting these pivot shafts 20,21 and cylindrical bar 10. Suitable bushings (not shown) are provided as needed to allow pivot shafts 20,21 and cylindrical bar 10 to rotate axially around the longitudinal centerline of pivot shafts 20,21. A handle 11, is attached to the cylindrical bar 10 perpendicular to the longitudinal centerline of the cylindrical bar 10. Cylindrical bar 10 is adjacent to, and in contact with pressure pad 9.

Figure 4:
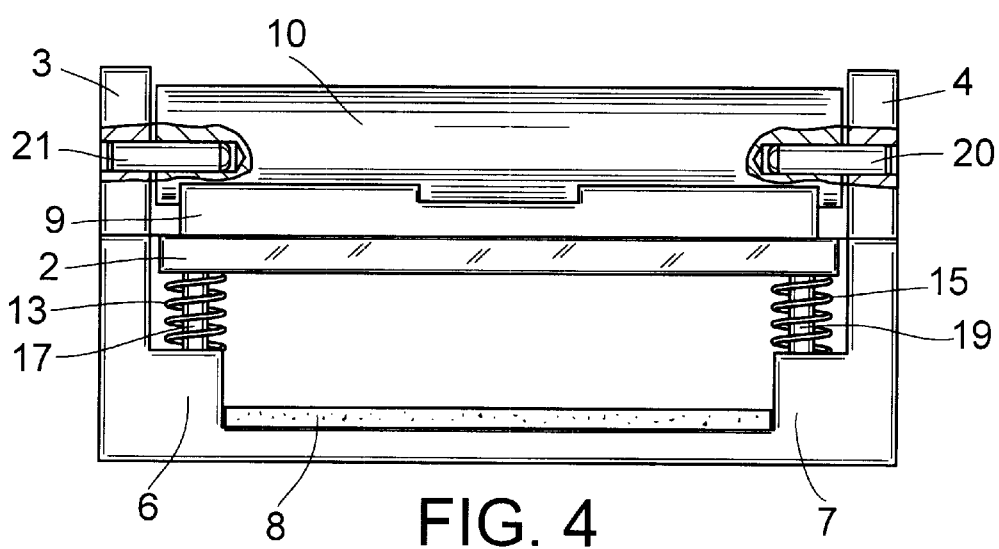
FIG. 4 shows a front view of the removal device.
Figure 5:
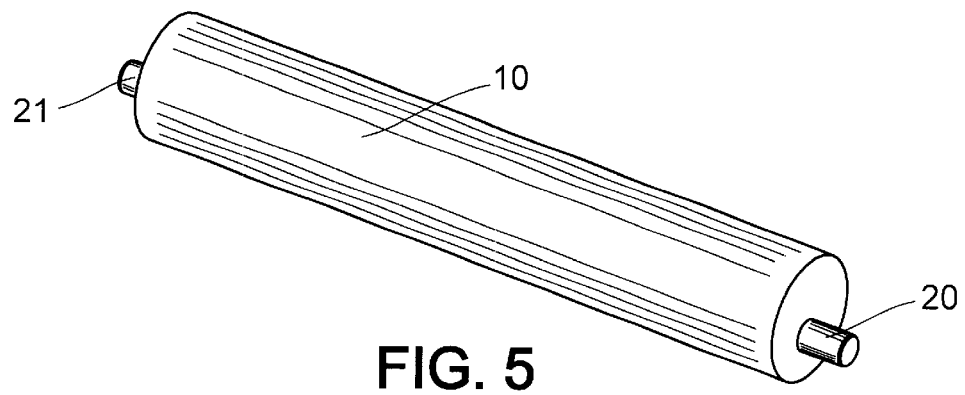
FIG. 5 shows perspective view of a cylindrical bar.
Figure 6:
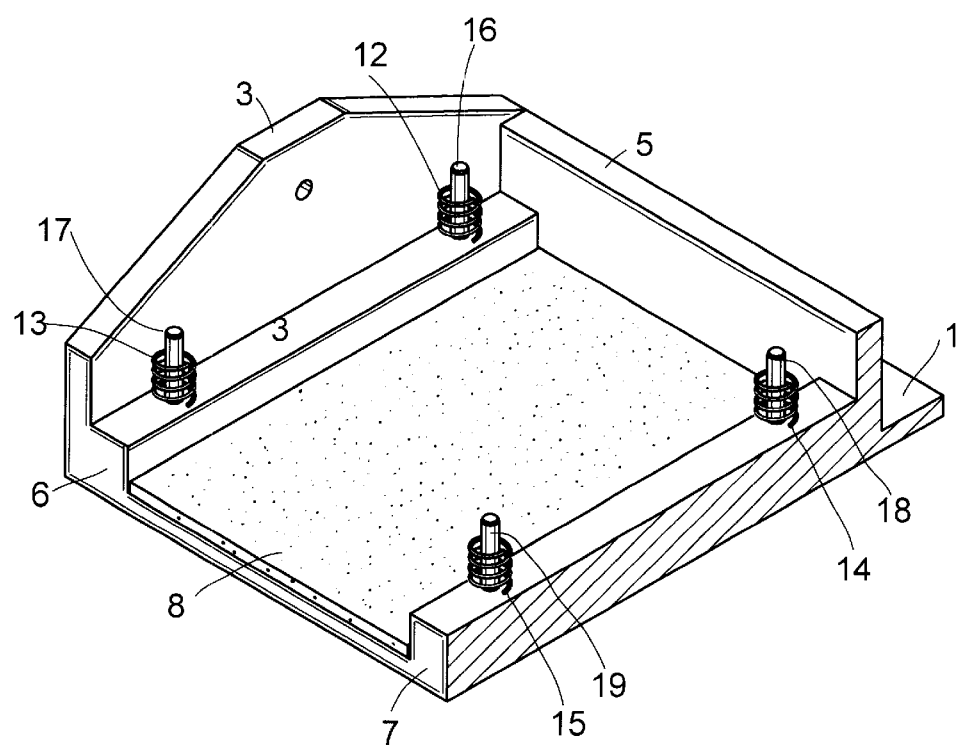
FIG. 6 shows a perspective view of a removal device without the moving plate and cylindrical bar sectioned approximately on the line A—A in FIG. 3
Figure 7A:
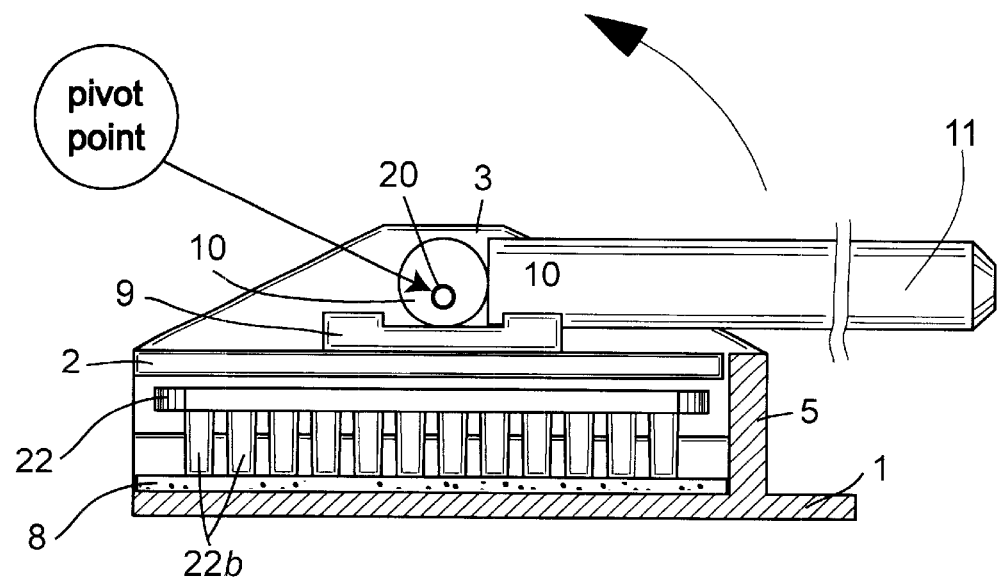
FIG. 7A shows the removal device during initial phase of operation.
Figure 7B:
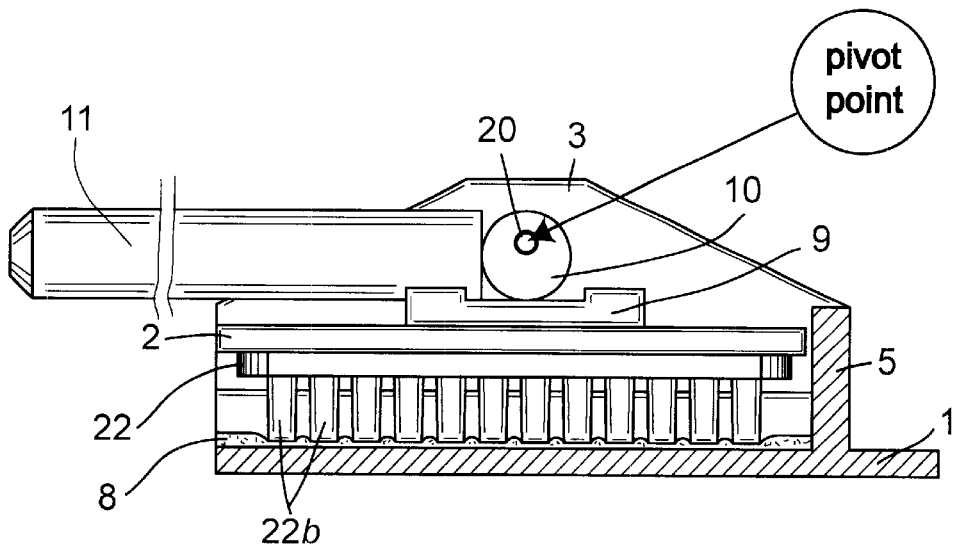
FIG. 7B shows the removal device during the final phase of operation.
Figure 9:
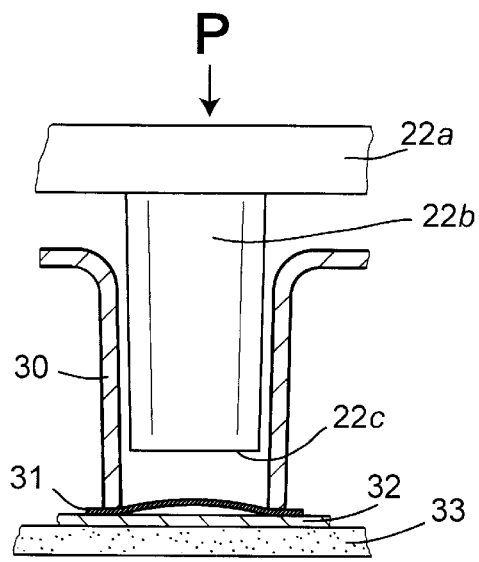
FIG. 9 shows a cross-section of initial phase of inserting the pushpin into the well.
Figure 10:
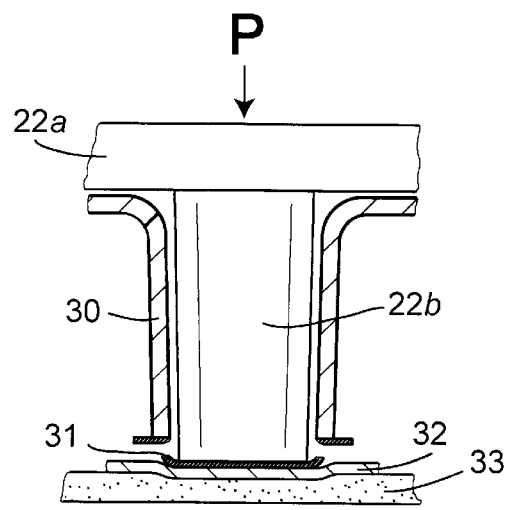
FIG. 10 shows a cross-section of the final phase of the pushpin removing a filter membrane and flattening it onto adhesive film.

In FIGS. 7A, 7B, 9 and 10 there is shown an operation of the removal device and a mechanism underlying the removal of filter membranes and their flattening onto adhesive film. First, the multi-well filtration plate is placed onto a piece of adhesive film 32 so that it is sticking to all filter membranes 31 in the plate. Then the pusher 22 is positioned above the filtration plate so that the pushpins are aligned with corresponding wells of the filtration plate such as to accommodate the insertion of the pusher 22 into the filtration plate (FIG. 9). The filtration plate with the pusher is disposed onto elastic pad 8 inside the removal device. As shown in FIG. 7A, moving the handle 11 approximately 180 degrees in a radial motion around the longitudinal center-line of pivot shafts 20,21, causes the cylindrical bar 10 to rotate in an eccentric motion, thus imparting a linear force to movable plate 2. FIG. 7B shows the device in its fully actuated state. As the handle 11 is moved back to its starting position, compression springs 12,13,14,15 return the movable plate 2 to its starting position. FIG. 4 illustrates, that pressure P is applied to the pusher 22 so that the pushpin 22b extends deeper into the well 30 to push onto the filter membrane 31, break it from the well 30 and flatten it against the adhesive film 32 supported by elastic pad 8.

Figure 8:
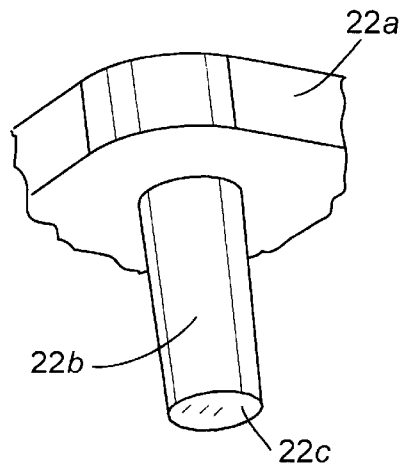
FIG. 8 shows a perspective view of a single pushpin from the pusher.

Referring to FIG. 8, the pushpin 22b comprises a flat face 22c to distribute an even, non-damaging, pressure over the entire area of the removed portion of the filter membrane.

The flat face 22c is preferred to have a round shape to match the shape of the filter membrane. To break a free section of the filter membrane 31 from its part which is bound to the well 30, the pushpin 22b is preferred to have a cylindrical shape, but can be of any other configuration. After completing a membrane-removing procedure, the membrane-backed plate with plugged-in pusher plate is removed from the membrane-removing device. After that adhesive support with individual membranes attached to it is pealed of the membrane-backed plate.

Figure 11:
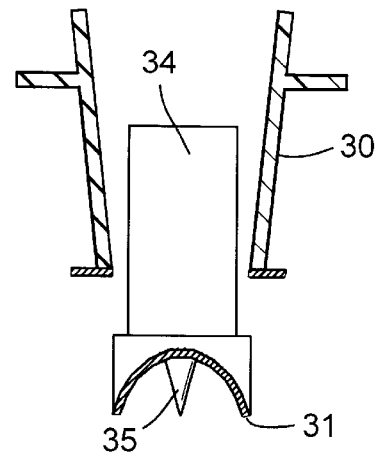
FIG. 11 shows an undesirable operation of one embodiment of the prior art.

FIG. 11 shows an undesirable operation of a filter punch 34 of the prior art which has in the center a conically shaped piercing member 35 which is designed to punch the filter membrane 31 from the well 30. However, piercing damages the filter membrane 31 and destroys the integrity of biological samples retained by it during removal. It is obvious that such a construction cannot be utilized to flatten the filter membrane 31 onto the adhesive film 32.

Our invention provides researchers who use filtration plates with the tool that facilitates collection, analysis and storage of multiple filter membranes after completing the experiment. This system is alternative to laborious and tedious single-pin manual membrane removal procedure that causes damage to membranes which, in turn, results in a loss of valuable experimental data. In addition, the system is user-friendly and does not require any specific training on the part of the operator. Furthermore, our system allows shortening of the filter removal time and thus makes this an indispensable tool for investigators who perform high-throughput testing using filtration plates.

Accordingly, it is a principal object of the present invention to provide means and method for a non-destructive removal of filter membranes with deposited specimens from filter-bottom microplates.

It is a further object of the invention to provide means and method for immediate transfer of removed filter membranes onto adhesive support for retention.

It is a further object of the invention to provide means and method for simultaneous removal of all filter membranes from a plurality of wells and simultaneous transfer of all removed filter membranes onto adhesive support.

Other objects of the present invention, as well as particular features and advantages thereof, will be elucidated in, or apparent from, the following description and the accompanying drawings.

While the preferred embodiment of the invention has been shown in the drawings and is herein particularly described it will be understood by those skilled in the art that many modifications and variations can be made and that some features can be employed without others, all within the scope of invention, the invention is no way limited to the illustrated embodiment.

What is claimed is:

1. A pusher comprising a plurality of pushpins and two opposing pushing surfaces, pushpins are secured to and extended perpendicular from one of said opposing surfaces, said pushpins having a pushing flat face and having a side area and a vertical axis, said pushpins having a shape and size to permit said pushpins to pass through wells to reach filters secured at the bottom of the wells, said flat face having substantially the same size and shape as a section of the filter to be punched the pushpins providing a means for punching the filter to simultaneousley provide a plurality of samples of the filter.

2. The pushpin of claim 1 wherein pushpin is providing a means to break a portion of the filter from its part which is secured to the bottom of the well.

3. The pushpin of claim 1 wherein said pushpin is providing a means to flatten the filter onto adhesive film.

* * * * *